United States Patent
Nashed (10) Patent No.: US 10,086,166 B1
(45) Date of Patent: Oct. 2, 2018

(54) DEMAND GAS FLOW VALVE APPARATUS

(71) Applicant: Ramses Nashed, Tierra Verde, FL (US)

(72) Inventor: Ramses Nashed, Tierra Verde, FL (US)

(73) Assignee: Sedation Systems, LLC, Clearwater, FL (US)

( * ) Notice: Subject to any disclaimer, the term of this patent is extended or adjusted under 35 U.S.C. 154(b) by 359 days.

(21) Appl. No.: 14/843,500

(22) Filed: Sep. 2, 2015

Related U.S. Application Data (63) Continuation-in-part of application No. 14/479,843, filed on Sep. 8, 2014, which is a continuation of application No. 12/658,019, filed on Feb. 1, 2010, now Pat. No. 8,826,905.

(Continued)

(51) Int. Cl.
*A61M 16/20* (2006.01)
*A61M 16/00* (2006.01)
(Continued)

(52) U.S. Cl.
CPC ...... *A61M 16/208* (2013.01); *A61M 16/0003* (2014.02); *A61M 16/06* (2013.01);
(Continued)

(58) Field of Classification Search
CPC .. A61B 5/14503; A61B 5/4839; A61M 16/00; A61M 16/0009; A61M 16/0051;
(Continued)

(56) References Cited

U.S. PATENT DOCUMENTS 3,556,097 A    1/1971  Wallace
3,800,825 A *  4/1974  Zoll .................. A01K 7/06
                                            119/72.5

(Continued)

FOREIGN PATENT DOCUMENTS

GB    2162757 A    2/1986
WO    97/00092 A1  1/1997

OTHER PUBLICATIONS

Zier et al., Case Series of Nurse-Administered Nitrous Oxide for Urinary 10 Catheterization in Children. Anesthesia & Analgesia. 2007. vol. 104 (No. 4): 876-879.

(Continued)

*Primary Examiner* — Annette Dixon
(74) *Attorney, Agent, or Firm* — Nilay J. Choksi; Smith & Hopen, P.A.

(57) ABSTRACT

A gas flow valve assembly. The assembly includes a cylindrical housing and a resiliently-biased valve supported substantially centrally within the housing. In the default or "off" condition, the resilient bias causes the valve to be seated on a valve seat shutting off axial flow of gas through the valve housing. When the patient breathes, negative pressure is applied to one side of the valve effective to sufficiently overcome the resilient bias imposed on the valve to move the valve off the valve seat axially (or otherwise open in another direction) within the housing, thereby allowing flow of gas through both the valve seat and the valve housing, and into the breathing circuit connected thereto. When the patient's breathing pauses and begins to exhale, the valve bias returns the valve to its default or off condition shutting off flow of gas through the valve.

19 Claims, 6 Drawing Sheets

Related U.S. Application Data (60) Provisional application No. 62/070,670, filed on Sep. 2, 2014.

(51) Int. Cl.
  *A61M 16/06* (2006.01)
  *A61M 16/12* (2006.01)
  *A61M 16/10* (2006.01)
  *A61M 16/08* (2006.01)

(52) U.S. Cl.
  CPC ...... *A61M 16/0891* (2014.02); *A61M 16/104* (2013.01); *A61M 16/122* (2014.02); *A61M 2016/003* (2013.01); *A61M 2016/0027* (2013.01); *A61M 2202/0208* (2013.01); *A61M 2202/0283* (2013.01); *A61M 2205/3334* (2013.01)

(58) Field of Classification Search
  CPC ............ A61M 16/0078; A61M 16/009; A61M 16/01; A61M 16/04; A61M 16/06; A61M 16/0605; A61M 16/0683; A61M 16/0816; A61M 16/0833; A61M 16/085; A61M 16/0875; A61M 16/0891; A61M 16/1005; A61M 16/1015; A61M 16/104; A61M 16/125; A61M 16/208; A61M 2005/1726; A61M 2039/1005; A61M 2202/0208; A61M 2202/0241; A61M 2202/0283; A61M 2205/11; A61M 2230/432; A61M 5/1723; A62B 18/02; A62B 9/006; Y10S 128/91; Y10S 128/912
  USPC ............ 128/203.12, 203.15, 203.25, 203.28, 128/203.29, 204.18, 205.12, 205.23, 128/205.24, 205.25, 206.21, 206.24, 128/206.26, 206.28, 207.11, 207.12, 128/207.14
  See application file for complete search history.

(56) References Cited

U.S. PATENT DOCUMENTS

| | | | |
|---|---|---|---|
| 3,960,148 A | 6/1976 | Dryden | |
| 4,112,940 A | 9/1978 | Parkes | |
| 4,248,218 A | 2/1981 | Fischer | |
| 4,265,239 A | 5/1981 | Fischer, Jr. et al. | |
| 4,312,339 A | 1/1982 | Thompson, Sr. | |
| 4,520,808 A | 6/1985 | LaBauve | |
| 4,527,558 A | 7/1985 | Hoenig | |
| 4,633,853 A * | 1/1987 | Prill | F16K 15/063 122/14.31 |
| 5,404,873 A | 4/1995 | Leagre et al. | |
| 5,485,835 A | 1/1996 | Vande Streek et al. | |
| 5,676,133 A | 10/1997 | Hickle et al. | |
| 6,273,087 B1 | 8/2001 | Boussignac et al. | |
| 6,578,571 B1 | 6/2003 | Watt | |
| 6,948,493 B2 | 9/2005 | Dunlop | |
| 7,849,853 B2 | 12/2010 | Grychowski et al. | |
| 7,900,633 B2 | 3/2011 | Sinha | |
| 8,333,198 B2 | 12/2012 | Sinha | |
| 8,336,549 B2 | 12/2012 | Nashed | |
| 8,550,076 B2 | 10/2013 | Nashed | |
| 8,726,900 B1 | 5/2014 | Nashed | |
| 8,826,905 B2 | 9/2014 | Nashed | |
| 8,826,909 B2 | 9/2014 | Nashed | |
| 2005/0103346 A1 | 5/2005 | Noble | |
| 2006/0032509 A1 | 2/2006 | Milles | |
| 2008/0251082 A1 | 10/2008 | Sinha | |
| 2008/0295845 A1 | 12/2008 | Nashed | |
| 2009/0235932 A1 | 9/2009 | Nashed | |
| 2010/0229861 A1 | 9/2010 | Nashed | |

OTHER PUBLICATIONS

International Search Report and Written Opinion for PCT/US2011/000166 (filed: Jan. 28, 2011) dated Nov. 1, 2011; Applicant: Nashed Ramses.

International Preliminary Report on Patentability for PCT.US2011/000166 (filed: Jan. 28, 2011) dated Feb. 1, 2010; Applicant: Nashed Ramses.

Further Examination Report for New Zealand IP No. 601551 dated Aug. 4, 2014; Applicant: Ramses Nashed.

Examination Report for New Zealand IP No. 601551 dated Apr. 26, 2013; Applicant: Ramses Nashed.

Extended Search Report for European Application No. 11737410.8-1662/2531248 (PCT/US2011000166) dated Nov. 19, 2014; Applicant: Nashed, Ramses.

* cited by examiner

DEMAND GAS FLOW VALVE APPARATUS

CROSS-REFERENCE TO RELATED APPLICATIONS

This nonprovisional application is a continuation of and claims priority to U.S. Provisional Patent Application No. 62/070,670, entitled "Demand Gas Flow Valve Apparatus", filed Sep. 2, 2014 by the same inventor, and is a continuation-in-part of and claims priority to U.S. Nonprovisional patent application Ser. No. 14/479,843, entitled "Respiratory Face Mask and Breathing Circuit Assembly", filed Sep. 8, 2014 by the same inventor, which is a continuation of and claims priority to U.S. Nonprovisional patent application Ser. No. 12/658,019, entitled "Respiratory Face Mask and Breathing Circuit Assembly", filed Feb. 1, 2010 by the same inventor, now U.S. Pat. No. 8,826,905, all of which are incorporated herein by reference in their entireties.

BACKGROUND OF THE INVENTION

1. Field of the Invention

The present application relates generally to devices for delivering respiratory gas or gases in medical applications. More specifically, it relates to breathing circuit assemblies and specifically demand valves for use in administering gases, such as anesthesia inhalation agents, oxygen, air, or mixtures thereof, for medical purposes.

2. Brief Description of the Prior Art

The current inventor has previously taught a disposable anesthesia face mask assembly having a flexible hollow inflatable sealing cushion extending along substantially the entire peripheral edge of the mask shell or body member to prevent anesthesia gas or the like delivered through the gas portal on the mask from escaping and adversely affecting the surgical environment. The unique face mask assemblies disclosed in the related patents (e.g., U.S. Pat. No. 8,336, 549; U.S. Pat. No. 8,826,909; and U.S. Pat. No. 8,550,076) represent a significant advancement over the prior art because, inter alia, they are the only respiratory or anesthesia masks known in the art to include a pneumatic sealing cushion that extends over and under the chin portion of the patient's face and surprisingly, as a result of this unique arrangement, requires only a relatively simple single headstrap or band for maintaining the mask in a stable position even during long duration surgical procedures. Hence, the mask and headstrap assemblies taught in the previous patents are ideally suited for use during "sedation" anesthesia procedures where the patient breathes on his/her own.

The current inventor also has previously taught a disposable breathing circuit assembly preferably for use with the foregoing face mask having a cushion that extends over and under the chin portion of the patient's face (U.S. Pat. No. 8,826,905, which is incorporated herein by reference in its entirety).

A well-known safe and effective sedation anesthetic in gas inhalation form is nitrous oxide ($N_2O$). This compound, frequently called "laughing gas" or "happy gas," has been used medically for many years usually as an analgesic or "light sedative" to ease pain associated with trauma, childbirth or heart attacks, for example, or as a carrier for more potent anesthesia gases (e.g., desflurane, sevoflurane). Indeed, nitrous oxide is so safe, easy to handle, and readily available relatively inexpensively, it has been used as an anesthetic in dentistry since the 1800s.

When used by a dentist, nitrous oxide is typically administered through a continuous inhaler placed over the patient's nose, so that the patient's mouth can be worked on while the patient continues to inhale the gas. A full facemask, therefore, cannot be used in dentistry for such application.

In Judith L. Zier, M D. et al, "Case Series of Nurse-Administered Nitrous Oxide for Urinary 10 Catheterization in Children", Anesthesia & Analgesia, 104:876-879 (2007), the authors reported the use of $N_2O$ to "sedate" children undergoing a painful procedure in a hospital setting. Administration of the nitrous oxide was carried out using commercially available "dental" equipment to supply the $N_2O$ gas and to scavenge exhaled waste (through a nose mask). Thus, the authors reported that a "comfortable seal could be maintained . . . over the nose of the older child" (emphasis added). Nitrous oxide is only minimally metabolized in the human body. Accordingly, unless provision is made to collect or otherwise scavenge the breath of a patient exhaled through the mouth, build-up of exhaled $N_2O$ waste gas in the hospital environment using such "dental equipment" cannot reasonably be avoided.

Attempts have been made to solve these problems. For example, U.S. Pat. No. 4,527,558 to Hoenig discloses a system for delivering anesthetic gas to a patient from a gas mixing device through a combined breathing mask and a demand valve assembly. A demand valve is normally closed to the flow of gas therethrough, but is responsive to the vacuum caused by a patient breathing through the mask attached to the valve, to allow the passage of gas through the valve and mask assembly until the patient ceases to inhale, or begins to exhale.

When the patient exhales, the demand valve has already shut off the supply of anesthetic gas until the next inspiration cycle. In the Hoenig system, the combined mask and demand valve assembly (i.e., both units) is located remotely and distally at the end of a flexible supply hose or tube which, in turn, is connected to the gas mixing device. This enables the patient to hold the demand valve and mask assembly by hand and self-administer the aesthetic gas (e.g., typically a mixture of $N_2O$ and oxygen). In the system of Hoenig, a separate flexible tube attached to the output of the demand valve is connected to a surge tank or chamber for storing exhaled gas so as to ostensibly help prevent the exhaled gas from contaminating the room environment. The surge tank, in turn, is connected to a central vacuum system for scavenging the exhaled waste gas stored in the surge tank.

The foregoing anesthetic gas delivery and scavenging system according to Hoenig has several disadvantages. Because the demand valve and mask assembly is held by the patient, and the patient breathes through the demand valve and scavenging (exhalation) tubing and surge tank, these fixed non-disposable components of the system must be cleaned or sterilized after each patient use to avoid cross-contamination (i.e., only the face mask or insert is disposable). Additionally, because the patient must manually grasp the relatively bulky mask and demand valve assembly during gas administration, the demand valve, a relatively delicate mechanism, is susceptible of being damaged by being dropped or otherwise mishandled by the patient. Moreover, the scavenger or surge tank is of fixed volume and can be overwhelmed by vigorous exhalation causing venting and possible room contamination. Also, the surge tank tends to collect moisture which compromises its function and tends to promote growth of bacteria or other contagions. Finally, the surge tank includes a hydrophobic polyurethane resistance plug which may increase the difficulty of exhalation experienced by the patient.

Further, U.S. Pat. No. 8,726,900 to Nashed (current inventor) teaches a demand anesthetic gas delivery system with disposable face mask and breathing circuit. This system uses the same or similar "demand valve" as in Hoenig in its operation to control inspiration and exhalation. However, among other differences, the demand valve is located on a bracket or arm affixedly attached to the gas mixing device, i.e., as opposed to being mounted on the face mask.

Accordingly, what is needed is an improved and more efficient demand gas flow valve apparatus. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved "demand" gas flow valve for use in a respiratory delivery system is now met by a new, useful, and nonobvious invention.

A flow valve is provided for use in medical respiratory systems for delivering gas or a mixture of gases to a patient "on demand," i.e., in response to the negative pressure produced when the patient breathes through a face mask and breathing circuit. The valve is designed to be interposed between the breathing circuit inspiration port and the output of a "flowmeter" or gas mixing and delivery device.

In an embodiment, the current invention is a breathing circuit system for delivering gas from a supply of fresh gas (e.g., nitrous oxide, oxygen, mixtures thereof, etc.) to a patient or user thereof through a face mask. The system generally includes an inspiration lumen and a demand valve. The face mask is coupled to the proximal end of the inspiration lumen, the distal end of the inspiration lumen is coupled to the proximal end of the demand valve, and the distal end of the demand valve is coupled to the source of fresh gas. The proximal end of the demand valve is in fluid communication with the distal end of the inspiration lumen, and the distal end of the demand valve is in fluid communication with the supply of fresh gas. The demand valve is a one-way valve that is responsive to breathing by the patient or user, so it controls the flow of fresh gas through to the inspiration lumen. The demand valve includes a valve member and a resilient bias member (e.g., spiral or compression spring disposed around the stem, where the spring can withstand external pressure and forces until an "activating negative pressure" of about −1 cmH$_2$O to about −10 cmH$_2$O is present within the breathing circuit and/or demand valve). The valve member and resilient bias member are both disposed within the demand valve and are in communication with each other, such that they move congruent with one another. The demand valve has a closed position and an open position. The closed position is a default position for the valve in the absence of negative pressure in the inspiration lumen. In this position, fresh gas substantially cannot pass through the valve into the inspiration lumen. The open position occurs when the valve member and resilient bias member move axially when there is negative pressure in the inspiration lumen when the patient or user inspires gas through the face mask and inspiration lumen. In this position, fresh gas can pass through the valve into the inspiration lumen.

The demand valve may include a housing extending axially between the proximal and distal ends of the demand valve, defining an internal passage therein. Fresh gas can pass from the source into the inspiration lumen through the internal passage when the valve is open. In this case, at least a portion of the valve member moves axially within the internal passage. The internal passage is fully obstructed when the valve is closed; the internal passage is partially obstructed or not obstructed at all when the valve is open. The resilient bias member maintains the valve member in the closed position.

The demand valve may further include a transverse divider wall disposed within the housing and include a valve seat. The divider wall would divide the housing into a proximal compartment and a distal compartment on opposite sides of the divider wall. The internal passage includes an opening disposed through the divider wall, where the valve member fully obstructs the opening when the valve is closed.

The internal passage may also include arcuately-shaped flow passages disposed through the divider wall, where the valve member fully obstructs the arcuately-shaped flow passages when the valve is closed. Alternatively or in addition, the internal passage may include supplemental flow passages disposed through the divider wall, where the valve member fully obstructs the supplemental flow passages when the valve is closed.

The valve member may include a piston and a stem extending axially from the piston through the opening from the proximal compartment into the distal compartment. The piston would be positioned in the proximal compartment directly adjacent to the valve seat when the valve is closed. The resilient bias member is positioned in the distal compartment of the demand valve and causes axial movement of the stem within the opening in the divider wall. The piston engages the valve seat to fully obstruct the internal passage when the valve is closed.

The demand valve may further include a retainer washer coupled to the stem in proximity to a distal tip of the stem. In this case, the proximal end of the resilient bias member engages or is otherwise disposed adjacent to the divider wall. The distal end of the resilient bias member engages or is otherwise disposed adjacent to the retainer washer, such that the resilient bias member is maintained on one end by the divider wall and on its opposite end by the retainer washer.

The demand valve may further include a sleeve extending distally from the divider wall into the distal compartment of the demand valve. The sleeve would surround the resilient bias member. The retainer washer would then contact the sleeve when the valve is open to prevent the valve member and resilient bias member from traversing further proximally when transitioning from the closed state to the open state.

In an embodiment, the valve stem includes a pair of tangs, each tang having a barb that defines a retention ledge. The retainer washer would be coupled to the stem by sitting on the retention ledge of each tang. The barb of each tang would be disposed through a central aperture of the retainer washer.

The source of fresh gas in the system may further include a flowmeter and optionally a conductor and a pressure sensor in the source of fresh gas. The conductor would be electrically coupled to the pressure sensor and to the flowmeter. The conductor receives an over-inflation signal from the pressure sensor. The conductor would then transmit a signal to the flow meter to shut off to prevent over-inflation.

In a separate embodiment, the current invention is a demand gas valve apparatus. The valve apparatus generally includes a housing, a valve member disposed in the housing, and a resilient bias member (e.g., spiral or compression spring disposed around the stem, where the spring can withstand external pressure and forces until an "activating negative pressure" of about $-1$ cmH$_2$O to about $-10$ cmH$_2$O is present within the breathing circuit and/or demand valve)) disposed in the housing. An internal passage runs through the longitudinal axis of the housing between the housing's proximal and distal ends, such that gas can pass from its distal end to its proximal end via the internal passage. The valve member and resilient bias member are in communication with each other, such that they move congruent with one another. The demand valve has a closed position and an open position. The closed position is a default position for the valve in the absence of negative pressure along the proximal end of the housing. In this position, fresh gas substantially cannot pass from the distal end of the housing to the proximal end of the housing through the valve. Also in the closed position, the resilient bias member is not under any stress or force, such that the resilient bias member maintains the valve member in the closed position as the default position. The internal passage is fully obstructed by the valve member in this position, thus preventing the flow of gas therethrough. The open position occurs when the valve member and resilient bias member move axially when there is negative pressure along the housing's proximal end. In this position, fresh gas can pass from the distal end of the housing to the proximal end of the housing through the valve. Also in the open position, the resilient bias member is under a stress or force caused by the negative pressure. At least a portion of the valve member moves axially within the internal passage in this position. The internal passage is only partially obstructed by the valve member or not obstructed at all in this position, thus permitting flow of gas therethrough.

A transverse divider wall may be disposed within the housing and include a valve seat. The divider wall would divide the housing into a proximal compartment and a distal compartment on opposite sides of the divider wall. The internal passage includes an opening disposed through the divider wall, where the valve member fully obstructs the opening when the valve is closed.

The internal passage may also include arcuately-shaped flow passages disposed through the divider wall, where the valve member fully obstructs the arcuately-shaped flow passages when the valve is closed. Alternatively or in addition, the internal passage may include supplemental flow passages disposed through the divider wall, where the valve member fully obstructs the supplemental flow passages when the valve is closed.

The valve member may include a piston and a stem extending axially from the piston through the opening from the proximal compartment into the distal compartment. The piston would be positioned in the proximal compartment directly adjacent to the valve seat when the valve is closed. The resilient bias member is positioned in the distal compartment of the demand valve and causes axial movement of the stem within the opening in the divider wall. The piston engages the valve seat to fully obstruct the internal passage when the valve is closed.

A retainer washer may be coupled to the stem in proximity to a distal tip of the stem. In this case, the proximal end of the resilient bias member engages or is otherwise disposed adjacent to the divider wall. The distal end of the resilient bias member engages or is otherwise disposed adjacent to the retainer washer, such that the resilient bias member is maintained on one end by the divider wall and on its opposite end by the retainer washer.

A sleeve may extend distally from the divider wall into the distal compartment of the housing. The sleeve would surround the resilient bias member. The retainer washer would then contact the sleeve when the valve is open to prevent the valve member and resilient bias member from traversing further proximally when transitioning from the closed state to the open state.

The valve stem can include a pair of tangs, each tang having a barb that defines a retention ledge. The retainer washer would be coupled to the stem by sitting on the retention ledge of each tang. The barb of each tang would be disposed through a central aperture of the retainer washer.

Through the foregoing "demand" gas flow valve, it is thus an object of the present invention to provide a simplified and effective means for enabling a patient to self-administer gas, or mixtures of same, through a face mask and breathing circuit. Preferably, though not exclusively, the present invention advantageously may be employed to administer sedation gas to patients, including but not limited to, mixtures of nitrous oxide and oxygen.

In a separate embodiment, certain embodiments of the current invention can include any one or more, or even all, of the foregoing characteristics and still be within the scope of the current invention.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the new and improved demand gas flow valve apparatus according to the present invention may be practiced. It is to be understood that other embodiments may be utilized and structural changes may be made without departing from the scope of the invention.

As used in this specification and the appended claims, the singular forms "a". "an", and "the" include plural referents unless the content clearly dictates otherwise. As used in this specification and the appended claims, the term "or" is generally employed in its sense including "and/or" unless the context clearly dictates otherwise.

In an embodiment, the current invention is a demand gas flow valve apparatus, generally denoted by the reference numeral 10, and comprises a unitary functional assembly formed of tubular or hollow cylindrical housing 12, valve member 14, resilient biasing member 16 optionally in the form of a coil or spiral compression spring, and spring retainer washer 18.

Figures 1A, 1B, 1C:
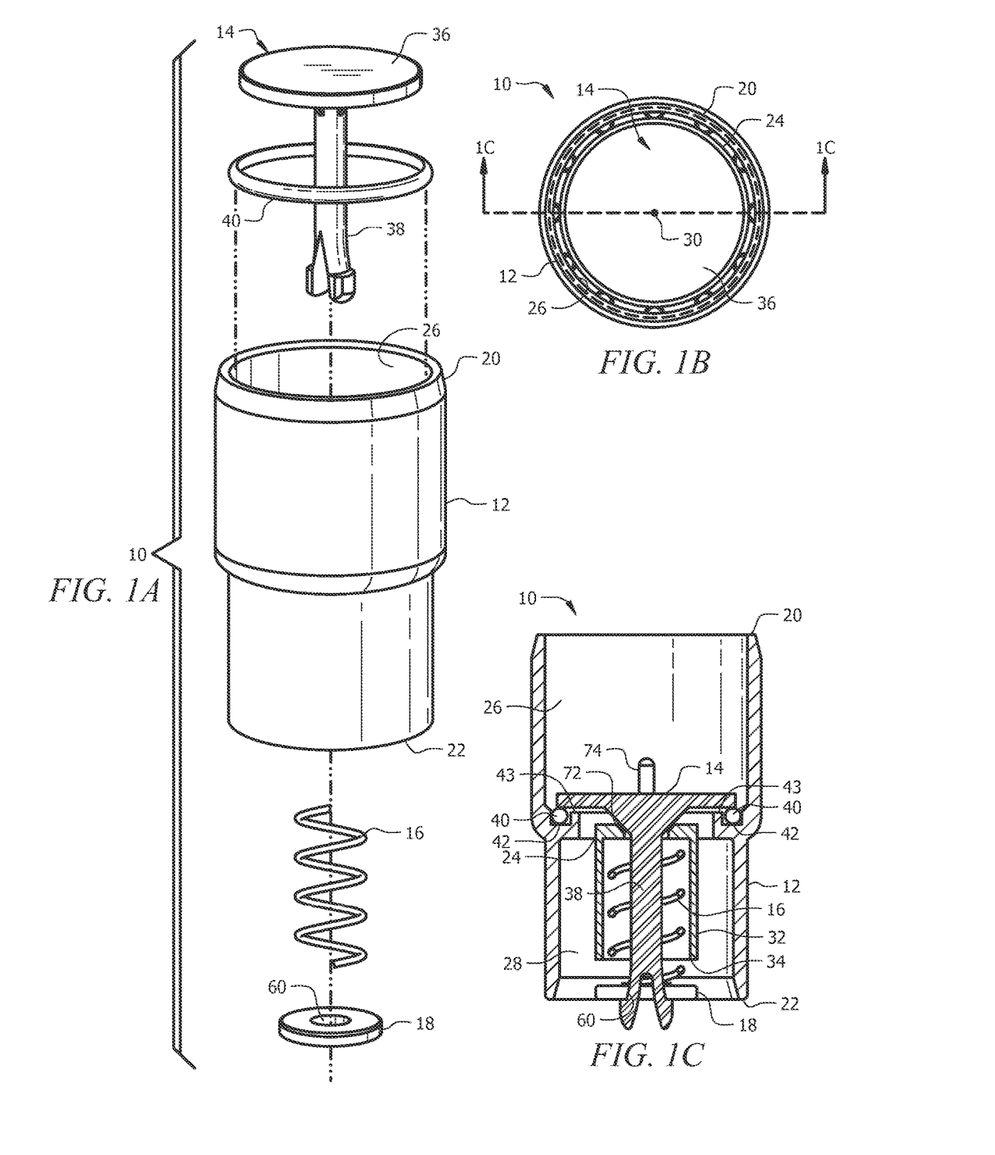
FIG. 1A is an exploded assembly view of a demand gas flow valve apparatus according to the present invention.
FIG. 1B is top plan view of the demand gas flow valve apparatus of FIG. 1A.
FIG. 1C is a cross-sectional elevational view taken along line B-B in FIG. 1B.

As seen in FIGS. 1A-IC, housing 12 has a substantially hollow interior, an open first end defined by peripheral edge 20, and an open second end defined by peripheral edge 22, where the first end and the second are on opposite ends of housing 12 with the substantially hollow interior formed therebetween. An integrally formed partition or divider wall 24 extends transversely (relative to the longitudinal extent of housing 12) and intermedially within the hollow interior of housing 12, separating the interior of housing 12 into first compartment 26 and second compartment 28, collectively compartments 26 and 28. In an embodiment, transverse divider wall 24 and compartments 26 and 28 are all coaxial with respect to an imaginary central axis 30 running longitudinally through housing 12 as viewed in FIGS. 1C and 3A. The terms "longitudinal," "coaxial," "axial," "axially," "radial," "transversely," or the like, as used herein shall mean with reference to this imaginary central axis 30 unless noted otherwise. It should be noted that these terms are relative terms of art, and the configuration of the current invention can be described in other ways, while still having the same or similar function and/or structure. Similarly, the term "proximal" is a relative term of art referring to a position closer to peripheral edge 20 or in that general direction; the term "distal" is a relative term of art referring to a position closer to peripheral edge 22 or in that general direction.

Various openings or flow passages are formed in transverse divider wall 24, as will be explained in more detail as this specification continues, to enhance fluid communication between first and second compartments 26 and 28, given the inclusion valve member 14, resilient biasing member 16, and retainer washer 18. Tubular and/or substantially hollow cylindrical sleeve 32, integrally formed with transverse divider wall 24, extends downwardly from the undersurface of transverse divider wall 24 coaxially within second compartment 28. Sleeve 32 terminates in peripheral end edge 34 defining a sleeve opening located within second compartment 28. Peripheral end edge 34 of sleeve 32 is spaced axially above peripheral edge 22 of the open second end of second compartment 28 of housing 12, substantially as depicted in FIGS. 1C and 3B. Sleeve 32 serves as housing or receptacle for a portion of an axially oriented, resiliently biased, gas flow valve assembly including valve member 14, resilient biasing member 16 preferably in the form of a coil or spiral compression spring, and spring retainer washer 18.

Figure 2A:
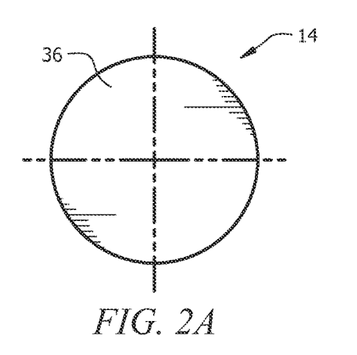
FIG. 2A is a top plan view of a disc valve component of a demand gas flow valve apparatus, according to an embodiment the current invention.
Figure 2B:
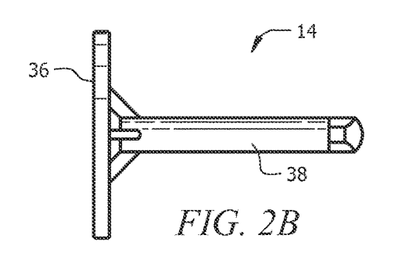
FIG. 2B is a right side view of the disc valve component of FIG. 2A.
Figure 2C:
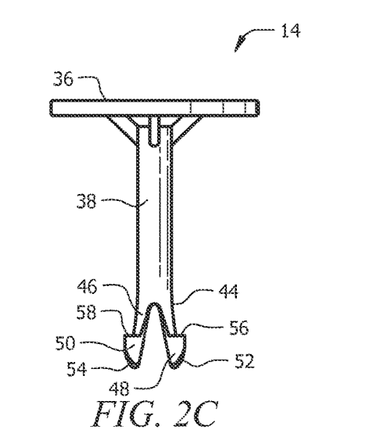
FIG. 2C is a bottom side view of the disc valve component of FIG. 2A.

Turning to FIGS. 2A-2D, valve member 14 includes valve disc 36 and integral, coaxial, elongated generally cylindrical valve stem 38 extending downwardly from the bottom surface of valve disc 36 substantially as depicted in FIG. 2C. Valve disc 36 has a thickness, is substantially circular in shape, and is substantially impermeable. As clearly visible in FIGS. 1B and 1C, the diameter of valve disc 36 is less than the inner diameter of first compartment 26 of housing 12, thereby resulting in an annular clearance space between the outer circumferential edge of valve disc 36 and the inside wall surface of first compartment 26, such that valve member 14 including valve disc 36 can be inserted into the substantially hollow interior of first compartment 26 of housing 12 (see FIG. 1C).

Figure 2D:
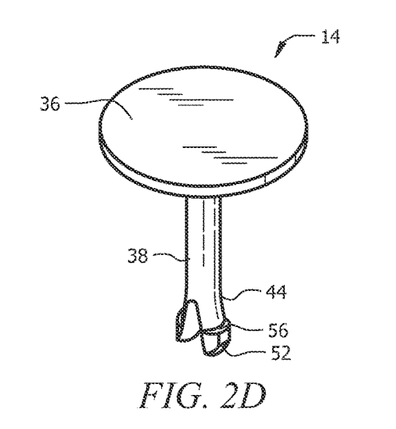
FIG. 2D is a top-left perspective view of the disc valve component of FIG. 2A.
Figure 4:
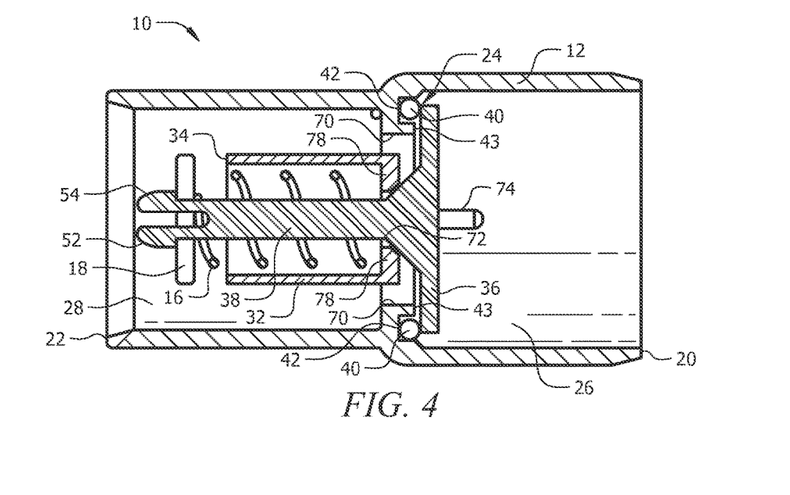
FIG. 4 is a cross-sectional perspective view showing a demand gas flow valve apparatus, according to an embodiment of the current invention, in a closed or default condition.
Figure 5:
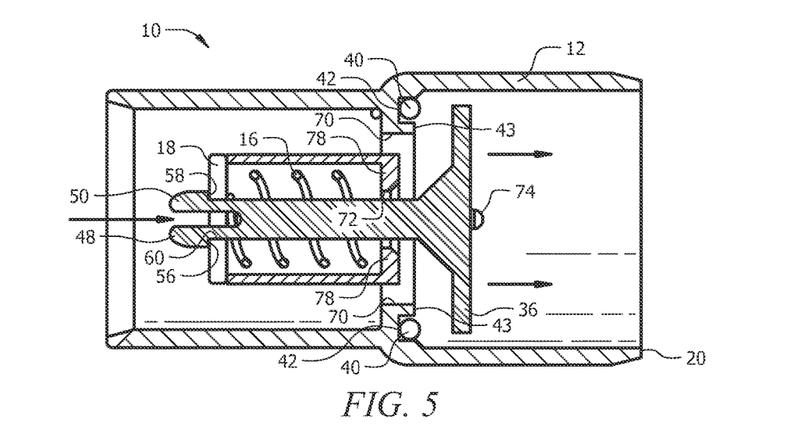
FIG. 5 is a cross-sectional perspective view showing the demand gas flow valve apparatus of FIG. 4 in an open or operative condition.

As best seen in FIGS. 2C and 2D, valve stem 38 terminates distally in a pair of bifurcations or tangs 44, 46. Tang 44 includes barb 48 defining cam surface 52 and retention ledge or shoulder 56. Similarly, tang 46 includes barb 50 defining cam surface 54 and retention ledge or shoulder 58. Tangs 44, 46 should be sufficiently flexible to be displaced radially toward one another in order to allow barbs 48, 50 including cam surfaces 52, 54 to be inserted through central opening 60 provided in spring retainer washer 18 (FIGS. 1A, 1C, 4 and 5). The flexible tangs then radially "spring back" firmly capturing, locking, or otherwise securing retainer spring washer 18 on the distal extremity of stem 38 via retention ledges 56, 58 on tangs 44, 46, substantially as depicted in FIGS. 1C, 4, and 5. The longitudinal or axial length of valve stem 38 typically is greater than the longitudinal or axial length of sleeve 32 to allow for sufficient axial travel of retainer washer 18 during operation of the valve apparatus 10. This mechanism will become clearer as this specification continues.

Figure 3A:
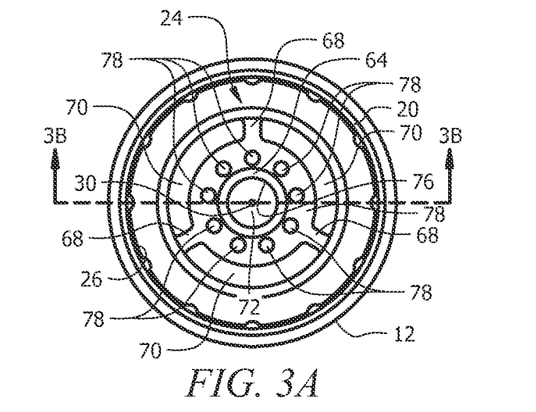
FIG. 3A is a top plan view of a valve housing component of the demand gas flow valve apparatus of FIG. 1A.
Figure 3B:
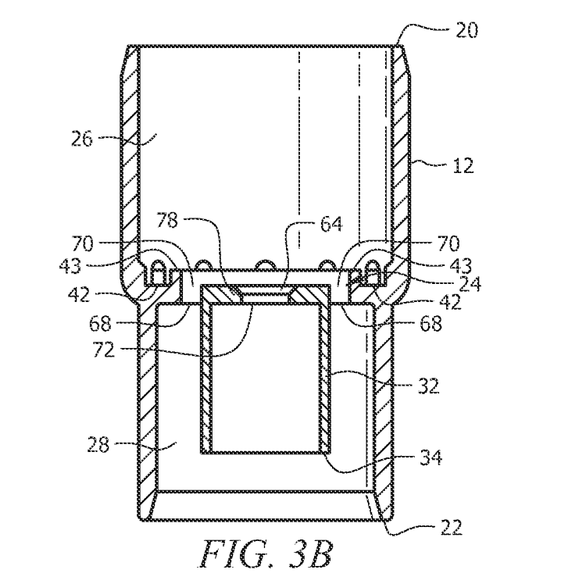
FIG. 3B is a cross-sectional elevational view taken along line A-A in FIG. 3A.

Now referring to FIGS. 3A and 3B, transverse divider wall 24 includes central hub portion 64, coaxial outer annular or ring portion 66, and radially extending rib portions 68 connected respectively between hub portion 64 and outer ring portion 66. In an embodiment, as depicted in FIG. 3A, three (3) rib portions 68 are disposed and angularly spaced apart about 120° with respect to one another, though any suitable number of rib portions 68 are contemplated herein at the appropriate angles with respect to each other, such that they are substantially equally spaced along the outer circumference of central hub portion 64 and the inner circumference of outer ring portion 66. By this arrangement, a corresponding series of three (3) arcuately-shaped "flow" passages 70 are formed in divider wall 24 between rib portions 68, respectively, the centers of which passages 70 are spaced apart about 120° with respect to one another, substantially as shown in FIG. 3A. It should be appreciated, however, that if the number of rib portions 68 are altered as in alternate embodiments of the current invention, then the number and angles of passages 70 would undergo a corresponding change.

Hub portion 64 includes coaxial central opening or cylindrical passage 72 that has any suitable size and shape for receiving valve stem 38 in snug sliding relationship (FIGS. 1C, 4, and 5).

Optionally, in an embodiment, hub portion 64 further includes a series of nine (9) substantially evenly spaced supplemental flow passages 78 arrayed circumferentially, as best depicted in FIG. 3A. As discussed in more detail below, supplemental flow passages 78 provide enhanced fluid communication between the interior of sleeve 32 and the interior of first compartment 26 of housing 12. As viewed in FIGS. 1C and 3B, the substantially flat top surfaces of central hub portion 64, coaxial outer ring portion 66, and radially extending rib portions 68 are substantially coplanar with respect to each other, thus collectively forming a substantially flat valve seat structured to be engaged by the substantially flat underside of valve disc 36 (see FIG. 1C).

To assemble the gas flow control valve 10 according to certain embodiments of the invention, valve stem 38 of valve member 14 is inserted axially into and through central opening 72 of hub portion 64 of transverse divider wall 24 until the bottom surface of valve disc 36 rests on the substantially flat valve seat (formed of the substantially flat top surfaces of central hub portion 64, coaxial outer ring portion 66, and radially extending rib portions 68) of transverse divider wall 24 (FIG. 1C).

With valve stem 37 now extending through sleeve 32, resilient bias member 16 (e.g., compression spring) can then be inserted into sleeve 32 via the open distal end of second compartment 28. Resilient bias member 16 should have a width or diameter that is larger than the width of valve stem 32, such that inserting resilient bias member 16 into sleeve 32 positioned resilient bias member 16 around valve stem 38.

Resilient bias member 16 can then be held in place by fitting the retainer washer 18, optionally underneath (distal) sleeve 32. This can be accomplished by flexing tangs 44, 46 radially toward one another to allow for retainer washer 18 to be inserted over retainer barbs 48, 50 via the action of cam surfaces 52, 54 engaging retainer washer 18 through central opening 60 of retainer washer 18 until retention ledges 56, 58 of retainer barbs 48, 50 engage the lower/distal surface of retainer washer 18 whereupon tangs 44, 46 are allowed to flex back to their original stable condition, thus locking retainer washer 18 in place. This resulting position of retainer washer 18 secured in place can be seen in FIGS. 1C, 4 and 5. As so assembled, resilient bias member 16 has a proximal end engaging the underside of transverse divider wall 24 at the proximal end of sleeve 32. Resilient bias member 16 also has a distal end engaging retainer washer 18 outside of sleeve 32. Retainer washer 18 is locked in place along the distal end of valve stem 38 via the retention ledges 56, 58, of barbs 48, 50, substantially as depicted in FIGS. 1C and 4.

Still referring to FIGS. 1C and 4, the assembled gas flow valve 10 normally reposes in the "closed" or default condition where fluid or gas flow from second compartment 28 proximally into first compartment 26 is prevented by the action of resilient bias member 16 (compression spring) applying a distal biasing axial force through retainer washer 18 and valve stem 38, where the force is sufficient to maintain substantially flat valve disc 36 seated on the substantially flat valve seat of divider wall 24. Under this "closed" or default condition, the seated valve disc 36 blocks flow of gas through arcuately-shaped flow passages 70 and supplemental flow passages 78 in divider wall 24.

In accordance with the present invention, gas flow valve apparatus 10 is intended for use in medical respiratory systems and more specifically, is intended to operate as a "demand" valve responsive to the breathing action of a patient when gas flow valve apparatus 10 is connected between a conventional face mask and breathing circuit, for example, and/or alternatively a conventional flowmeter capable of suitably providing a source of gas, or mixture of gases, to be inspired by the patient. The face mask may be any suitable face mask known in the art, for example including, but not limited to, the face masks taught by the current inventor in U.S. Pat. No. 8,726,900; U.S. Pat. No. 8,336,549; U.S. Pat. No. 8,826,905; U.S. Pat. No. 8,826,909; and U.S. Pat. No. 8,550,076.

Figure 6:
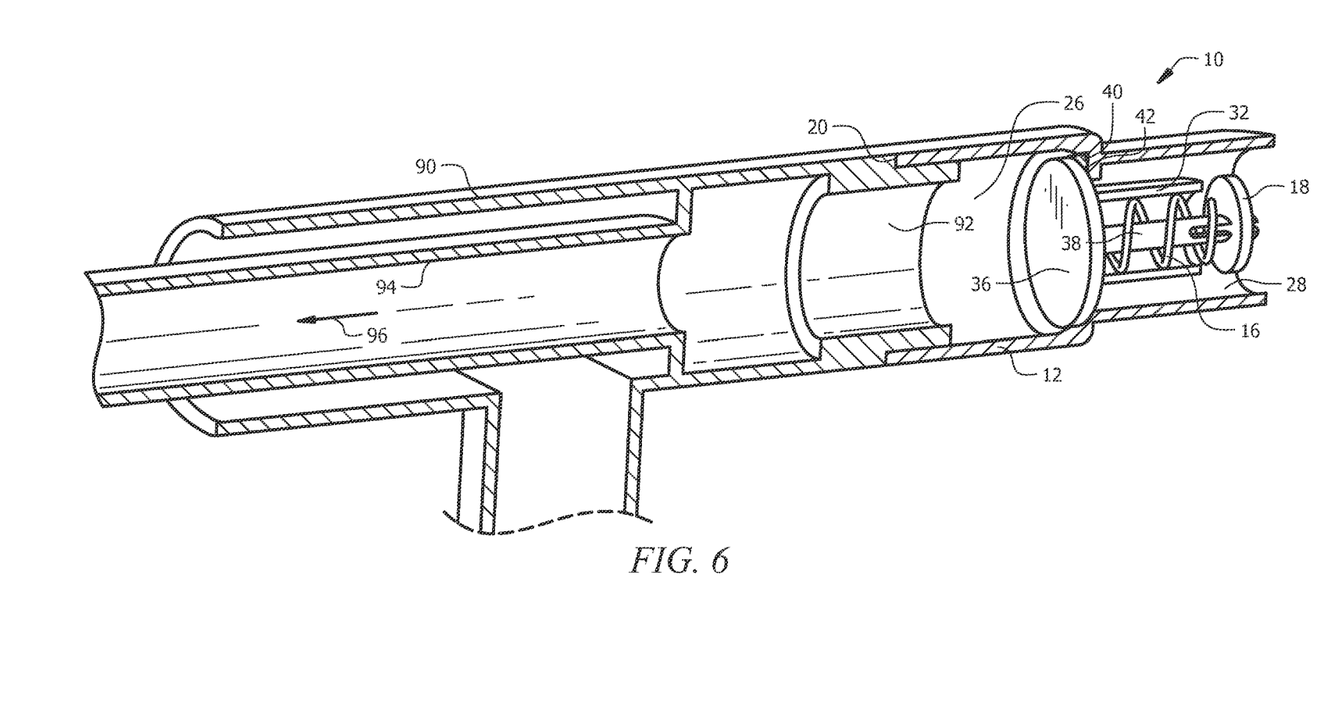
FIG. 6 is a cross-sectional perspective view showing an assembly, according to an embodiment of the current invention, including a demand gas flow valve apparatus attached to a portion of a breathing circuit T-connection.
Figure 7:
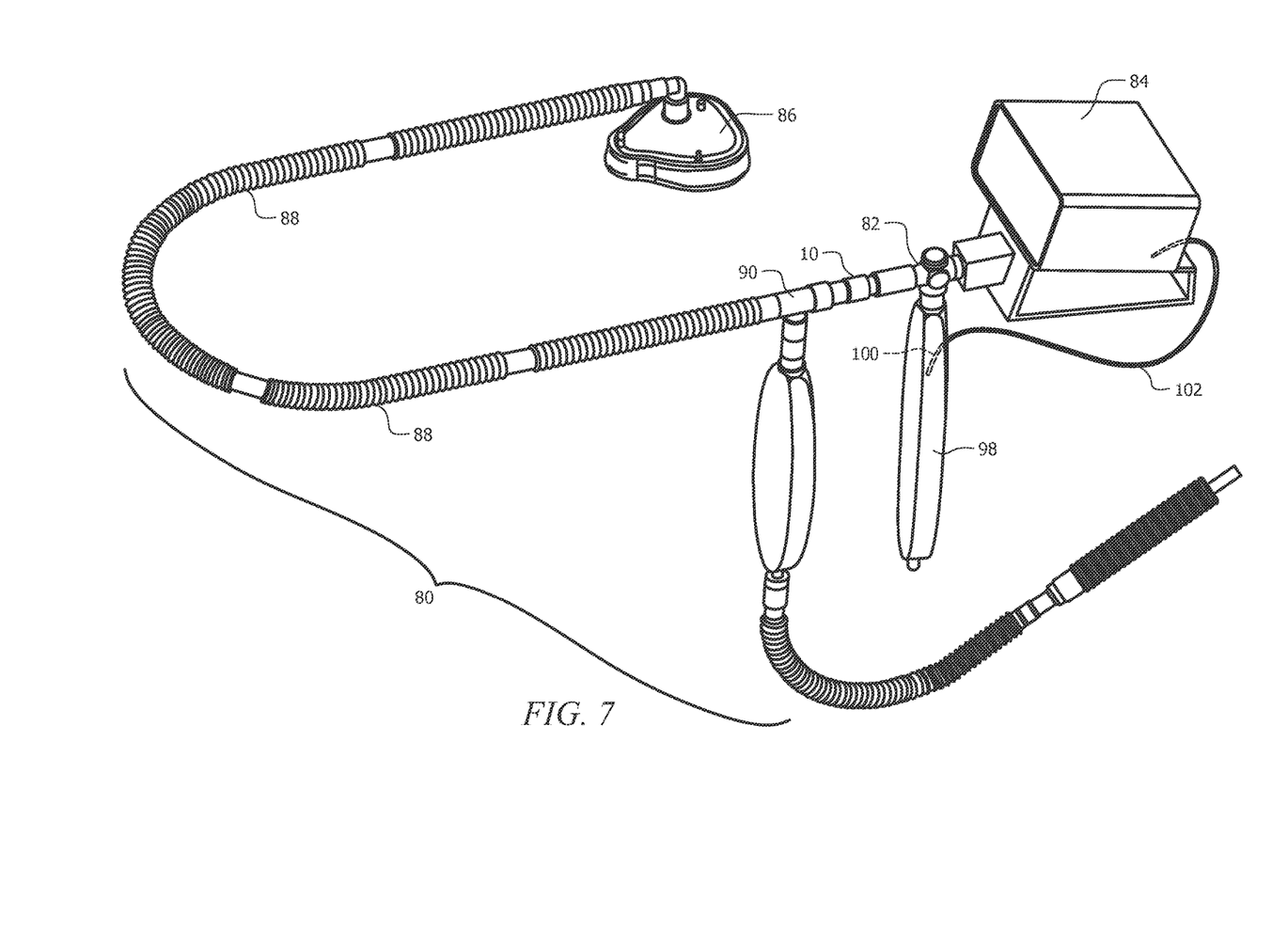
FIG. 7 is a perspective view schematically showing a demand gas flow valve interposed between a flowmeter and a breathing circuit and face mask set, according to an embodiment of the current invention.

In such an arrangement according to certain embodiments of the current invention, schematically depicted in FIGS. 6 and 7, gas flow valve apparatus 10 is shown interposed between breathing circuit 80 and output nozzle 82 of flowmeter 84. In other words, valve apparatus 10 is coupled directly or indirectly to breathing circuit 80 on its proximal end and to flowmeter 84 on its distal end via output nozzle 82 of flowmeter 84.

Breathing circuit 80, in turn, includes face mask 86 on its proximal-most end, flexible main limb 88 extending distally therefrom, and a branched T-connecter 90 coupling main limb 88 with valve apparatus 10. More specifically, the distal branch of T-connector 90 is connected in a fluid tight manner to first compartment 26 of gas flow valve housing 12 via any suitable adaptor or connector, for example tubular connector 92 (FIG. 6). By this arrangement, inspiration lumen 94 provided inside T-connector 90 is maintained in direct fluid communication with first compartment 26 defined by housing 12 of valve apparatus 10, as clearly seen in FIG. 6. Likewise, the opposed distal end or second compartment 28 of housing 12 likewise can be suitably connected to nozzle 82 via any suitable adaptor or connector.

Breathing circuit 80 can be any suitable breathing circuit known in the art, for example the breathing circuit disclosed in U.S. Pat. No. 8,826,905 entitled "Respiratory Face Mask and Breathing Circuit Assembly", issued to the current inventor, which is incorporated herein by reference in its entirety. Flowmeter 84 can be any suitable flowmeter known in the art, for example the flowmeter from ACCUTRON, Inc. (Phoenix, Ariz.) or the PORTER INSTRUMENT DIVISION OF PARKER HANNIFIN CORPORATION (Hatfield, Pa.).

In operation, inspiration or inhalation by the patient through breathing circuit 80, specifically face mask 86 (FIG. 7), causes any gas remaining in the inspiration lumen of main limb 88, T-connector 90, and first compartment 26 of valve apparatus 10 to be drawn proximally in the direction of arrow 96 (see FIG. 6) through lumen 94 of T-connector 90. This action momentarily creates a vacuum or negative pressure inside first compartment 26 of valve housing 12 sufficient to overcome the biasing spring force imposed by resilient bias member 16 (e.g., compression spring) against retainer washer 18. When and as this occurs, valve stem 38 is caused to travel proximally axially within central passage 72 of central hub portion 64, thus also lifting valve disc 36 off the valve seat on transverse divider wall 24 (compare FIG. 4 to FIG. 5 as resilient bias member 16 compresses and valve disc 36 is pushed off of the valve seat).

The biasing force of resilient bias member 16 required to normally maintain valve disc 36 on its valve seat until and unless a suitable "activating negative pressure" is present in first compartment 26 is a design variable dependent upon many factors including, but not limited to, the dimensions of the valve apparatus, the age and size of the patient, the force of breathing, and so on. Generally, for purposes of practicing embodiments of the present invention, for an average adult patient breathing normally through a connected conventional breathing circuit and or mask, it has been found that such suitable activating negative pressure can be in the range of about −1 $cmH_2O$ to about −10 $cmH_2O$.

As shown in FIG. 5, such axial translation of valve disc 36 continues until retainer washer 18 engages or abuts peripheral end edge 34 of sleeve 32. This can be denoted as the "fully open" position/condition of gas flow valve apparatus 10. During such movement of the valve disc 36, fresh gas can enter second compartment 28 of valve housing 12 via flowmeter output nozzle 82. The fresh gas can enter second compartment 28 of valve housing 12 by flowing through arcuately-shaped flow passages 70 and/or supplemental flow passages 78 in hub portion 68 of transverse divider wall 24.

Additionally, inasmuch as valve disc 36 now is lifted off the valve seat defined by divider wall 24, gas flowing through arcuately-shaped flow passages 70 and/or supplemental flow passages 78 passes through the clearance space between the outer circumferential edge of valve disc 36 and the inner wall surface of first compartment 26 (see FIG. 5).

During inhalation by the patient, flow of fresh gas continues to flow through lumen 94 in the direction of arrow 96 (see FIG. 6), through the inspiration passage/lumen in main limb 88 of breathing circuit 80, and through face mask 86. Upon inspiration, when the patient pauses before exhalation, and during exhalation, the negative pressure in lumen 94 and first compartment 26 of valve housing 12 dissipates, allowing resilient bias member 16 to axially return or push retainer washer 18, valve stem 38, and valve disc 36 to their "default" or "closed" position/condition, which can be seen in FIG. 4.

As can be seen in FIGS. 4-5, when valve apparatus 10 is in a closed position (FIG. 4), a spaced distance (unlabeled but shown) exists between retainer washer 18 and sleeve 32, specifically between retainer washer 18 and peripheral end edge 34 of sleeve 32. In this closed position, valve disc 36 sits on or abuts the valve seat of transverse divider wall 24 (i.e., there is minimal or no spaced distance between valve disc 36 and transverse divider wall 24), such that valve disc 36 substantially seals off first compartment 26 from second compartment 28, substantially prohibiting fluid from passing therethrough (minimal amounts of gas may potentially pass through the seal). Optionally, as can be seen in FIGS. 1C, 4, and 5, O-ring 40 can be positioned between valve disc 36 and the valve seat of transverse divider wall 24 when valve apparatus 10 is in the closed position in order to more effectively seal first compartment 26 from second compartment 28. O-ring 40 may be seated in a radially outer annular channel, generally denoted by the reference numeral 42, defined by a circumferential, inner radial array of evenly-spaced up-standing nubs 43. Channel 42 and nubs 43 can be seen clearly in FIGS. 3B, 4, and 5.

When valve apparatus 10 is in an open position (FIG. 5), retainer washer 18 sits on or abuts peripheral end edge 34 of sleeve 32 (i.e., there is no spaced distance between retainer washer 18 and transverse divider wall 24). In this open position, a spaced distance (unlabeled but shown) exists between valve disc 36 and sleeve 32, specifically between valve disc 36 and the valve seat of transverse divider wall 24, such that gas can flow from second compartment 28 to first compartment 26. As noted, in this open position, axial translation of valve disc 36 continues until retainer washer 18 engages or abuts peripheral end edge 34 of sleeve 32 so that valve member 14 and retainer washer 18 cannot traverse any further proximally.

Optionally, axial stop projections 74 may be disposed on the inner wall of first compartment 26 or otherwise extend from the proximal surface of divider wall 24, as seen most clearly in FIGS. 1C, 4, and 5. Projections 74 limit proximal travel of valve disc 36 and prevent housing 12 from being inserted onto the flowmeter nozzle of the adjacent breathing circuit 80 too far, where the distal edge of T-connector 90 would interfere with travel of valve disc 36 and thus jam travel of valve disc 36. As can be seen in FIGS. 4-5 specifically, projections 74 stop the travel of valve disc 36 at their proximal edges (see FIG. 5 in particular). Projections 74 may be disposed radially around the inner wall of first compartment 26. For example, three (3) of projections 74 may be disposed about 120o apart and relative to each other.

Optionally as noted previously, resilient bias member 16 may be a spiral, compression, or die spring. The spring should have a stiffness that is sufficiently low to not add to the work of breathing by the patient or user of valve apparatus 10; this stiffness can be such that the spring can withstand external pressure and forces until an "activating negative pressure" of about −1 $cmH_2O$ to about −10 $cmH_2O$ is present within the breathing circuit and/or demand valve). In this case, valve apparatus 10 would be able to open at a very low inspiratory pressure (e.g., −2.46 $cmH_2O$), and the mechanism of resilient bias member 16 may even be imperceptible by the patient or user. This spring would still close on expiration and thus prevent the free flow of gas out of face mask 86 that would contaminate the external environment until the next inspiration. If face mask 86 were to be temporarily lifted of the patient's face, then valve apparatus 10 would close and block flow of gas.

In certain embodiments, during the foregoing operation of the "demand" gas flow valve apparatus 10, flowmeter 84 continuously supplies fresh gas to the inspiration bag or gas reservoir 98 located distal and adjacent to output nozzle 82 of flowmeter 84 (see FIG. 7). In order to prevent the reservoir bag 98 from being overinflated during long pauses between use of breathing circuit 80 and mask 86 by the patient or user thereof, pressure sensor 100 can be installed in bag 98 and conductor 102 may be used to transmit an "off" control signal to the control panel (not shown) inside flowmeter 84, thereby shutting off flowmeter 84 before any such over-inflation occurs. When the patient or user again breathes through the apparatus of FIG. 7, gas flow valve apparatus 10 opens, gas flows out of reservoir bag 98 and through valve apparatus 10 and breathing circuit 98, so that the pressure in reservoir bag 98 can decrease sufficiently to null the sensor "off" control signal and also transmit an "on" control signal to the control panel for flowmeter 84 to initiate the next cycle.

In an embodiment of the current invention, demand gas flow valve apparatus 10 may be fabricated of durable molded polymeric and metallic materials. Optionally, housing 12, transverse divider wall 24, and spring retainer sleeve 32 can be molded as a unitary part from a suitable medical grade polymeric material. Valve member 14—including valve disc 36, valve stem 38, and guide rib members 42—may similarly be fabricated as a unitary part. The components are capable of easy assembly, as described in this specification above, leading to lower manufacturing cost and wider availability within the medical community. Preferably, the demand gas valve apparatus 10 is applied by being connected to known anesthesia breathing circuits or related devices and in this regard, can be fabricated to be in accordance with ISO Standard: 5356-1.

EXAMPLE

Without limiting the present invention, and merely for the sake of illustration, an example of demand gas valve apparatus 10 according to an embodiment of the current invention suitable for use in supplying medical gas to an "average adult" was constructed using conventional stereo-lithography (SLA) techniques having the following dimensions:

Length (axial extent): 39.69 mm (1.563 in.)
Inside diameter of first end: 22 mm (0.866 in)
Outside diameter of first end: 25.05 mm (0.096 in)
Outside diameter of second end: 22 mm (0.866 in)
Inside diameter of second end: 18.95 mm (0.746 in)
Wall thickness: 1.525 mm (0.059 in)
Valve disc diameter: 19.69 mm (0.775 in)
Thickness of valve disc: 1.524 mm (0.06 in)
Stem length: 24.09 mm (0.948 in)
Stem diameter: 3.302 mm (0.13 in)
Sleeve length: 13.208 mm (0.52 in)
Sleeve diameter: 11.049 mm OD×9.525 mm ID (0.435 in OD×0.375 in ID)
Retainer washer diameter: 11.049 mm OD×4.191 mm ID (0.435 in OD×0.165 in ID)

The foregoing demand gas valve apparatus example was designed to shift from the stable, closed position to the open position in the presence of an "activating negative pressure" in the first end chamber (first compartment 26) of about −2.46 cmH$_2$O. To accomplish this criterion, a commercially available spiral compression spring (i.e., resilient member 16) was utilized conforming to the following specifications:

Length: 19.05 mm (0.75 in)
Coil diameter: 7.95 mm OD×7.62 ID (0.313 in×0.300 in)
Number of coils: 5.2
Catalog No. LP 011C 04 S316
Vendor: Lee Spring Company, Brooklyn, N.Y.

The foregoing demand gas valve apparatus was bench-tested for functionality, as follows. The first end of the gas flow valve of the example valve apparatus was connected to the inspiration input port on the T-coupling of a NITROU-SEAL® full-face mask and breathing circuit set (Cat. No. CA0120MX-Small Adult-SEDATION SYSTEMS LLC, Clearwater, Fla.). The opposed second end of the gas flow valve of the exemplary embodiment was connected to the reservoir bag "Tee" output nozzle of a PORTER MXR Flowmeter having a bracket-mounted pressurized gas cylinder (oxygen). The apparatus was tested by having four human subjects (male and female adult, male and female teenager) breathe through the mask, breathing circuit, and gas flow valve after the oxygen flowmeter reservoir bag was flushed with oxygen and the MXR Flowmeter wand activated to 70% maximum flow. Each subject experienced normal breathing without restriction through the mask, breathing circuit and valve. When each subject lifted the mask off his/her face during testing interval, no leakage of oxygen flow was sensed through the breathing mask, and the flowmeter reservoir bag was observed to continue to inflate.

In summary, it will be appreciated from the foregoing that certain embodiments of the present invention provides a substantially improved, safe and effective demand gas flow valve apparatus capable of achieving one or more of the following benefits:

1. By utilizing the negative pressure generated during patient inspiration, the valve apparatus operates in a "demand mode" by opening to deliver fresh gas and then closing during breathing pause and exhalation, thus preventing the escape of gas into the room or the surrounding treatment area.
2. The valve apparatus can be utilized with continuous-flow nitrous/oxygen flowmeters to deliver titratable gas mixtures, e.g., mixtures of nitrous oxide and oxygen at "variable" concentrations between about 0% to about 70% on a demand basis. This is in contrast to conventional demand gas delivery systems which are capable of delivering only a fixed 50%-50% mixture.
3. The valve apparatus is compactly sized, disposable, and inexpensive to manufacture. Therefore, it can be efficiently employed with disposable breathing circuits (e.g. the NITROUSEAL® disposable breathing circuit) on a single-use (one-time) basis, in turn reducing the risk of cross-contamination from patient-to-patient.
4. The demand valve apparatus can be located at the distal end of a breathing circuit proximal to the juncture of the inspiration lumen of the circuit and the gas supply nozzle of a gas supply device (flowmeter), thereby obviating the necessity of mounting the demand valve on the patient's breathing mask.
5. The demand valve apparatus can be sold as a "kit" in a single package with a breathing circuit, or with a combination of a breathing circuit and a full-face mask. Alternatively, the demand valve apparatus can be sold alone and packaged separately for subsequent attachment to a breathing circuit.

Still other advantages and benefits of the present invention as well as any further manner of usage and operation of the present invention should be apparent from the foregoing specification without any further discussion.

Glossary of Claim Terms

Axial: This term is used herein to refer to relative direction along the longitudinal axis of the underlying structure.

Demand valve: This term is used herein to refer to a device that detects when a patient or user has inhaled a gas, and subsequently facilitates supplying fresh gas to that patient or user.

Directly adjacent: This term is used herein to refer to position of a component abutting or nearly abutting another component. An example of a component nearly abutting another component is the valve disc being positioned directly adjacent to the valve seat but with an O-ring positioned therebetween to add an additional seal.

Distal: This term is used herein to refer to a relative position of a component further from patient or user of the underlying device Fully obstruct: This term is used herein to refer to blocking or filling a passage or pathway to the extent that gas cannot pass freely therethrough.

Inspiration lumen: This term is used herein to refer to a cavity or channel in a breathing circuit through which gas flows when a patient or user thereof breathes in.

Internal passage: This term is used herein to refer to any path within the demand valve that would permit gas to flow therethrough when that path is open.

Negative pressure: This term is used herein to refer to a condition created when gas is removed from an enclosed area without replenishing that exhaust gas with new gas. Additionally, the term "activating negative pressure" refers to an amount of pressure that overcomes the resilient bias of the resilient bias member (e.g., spring) and causes the resilient bias member to actuate the valve member and thus open the valve apparatus.

Piston: This term is used herein to refer to a disk or cylinder that fits inside a hollow housing and moves within the housing under pressure.

Proximal: This term is used herein to refer to a relative position of a component closer to patient or user of the underlying device.

Resilient bias member: This term is used herein to refer to a component that has a stable position but can be manipulated (e.g., bent, compressed, expanded, etc.) in at least one direction, wherein the component exerts a force back to its stable position when it is manipulated.

Retainer washer: This term is used herein to refer to any structural component that prevents further movement of the valve member and resilient bias member when transitioning from a closed position to an open position.

Supply of fresh gas: This term is used herein to refer to any suitable structure that can provide a fluid. Typically, the gas (e.g., oxygen, nitrous oxide, etc.) can come from a tank or storage vessel that holds gas or liquid under pressure and provides that fluid when needed.

Valve member: This term is used herein to refer to a structural component of the underlying demand valve, where the component can provide a seal from gas passing therethrough.

Valve seat: This term is used herein to refer to a surface of the transverse divider wall on which a portion of the valve member can rest in order to provide a seal through which gas could not freely pass.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A demand gas valve apparatus, comprising:
a housing having a proximal end and a distal end, said housing defining a longitudinal axis and defining an internal passage extending between said distal end and said proximal end of said housing, such that gas can pass from said distal end to said proximal end through said internal passage;
a transverse divider wall disposed within said housing and including a valve seat, said transverse divider wall dividing said housing into a proximal compartment and a distal compartment located respectively on opposite sides of said valve seat,
said internal passage including an opening disposed through said transverse divider wall;
a valve member disposed within said housing and including a piston and a stem, wherein said stem extends axially from said piston through said opening from said proximal compartment into said distal compartment;
a resilient bias member disposed within said distal compartment of said housing and in communication with said valve member, such that said valve member and said resilient bias member move congruent with one another with said resilient bias member causing axial movement of said stem within said opening,
a retainer washer coupled to said stem in proximity to a distal tip of said stem,
wherein a proximal end of said resilient bias member engages or is otherwise disposed adjacent to said transverse divider wall,
wherein a distal end of said resilient bias member engages or is positioned directly adjacent to said retainer washer, such that said resilient bias member is maintained on its proximal end by said transverse divider wall and on its distal end by said retainer washer; and
a sleeve extending distally from said transverse divider wall into said distal compartment, said sleeve surrounding said resilient bias member,
said valve apparatus having a closed position and an open position, said closed position of said valve apparatus being a default position in the absence of negative pressure along said proximal end of said housing, such that gas cannot pass from said distal end to said proximal end through said internal passage of said housing,
said resilient bias member not being under any stress or force in said closed position, wherein said resilient bias member maintains said valve member in said closed position as said default position,
said piston positioned in said proximal compartment directly adjacent to said valve seat in said closed position, wherein said piston engages said valve seat to fully obstruct said opening of said internal passage in said closed position, thus preventing flow of gas through said internal passage,
said open position occurring due to axial movement of said valve member and said resilient bias member as a result of the presence of negative pressure along said proximal end of said housing, such that gas can pass from said distal end to said proximal end through said internal passage of said housing,
said resilient bias member being under a stress or force caused by said negative pressure in said open position,
wherein at least a portion of said valve member moves axially within said internal passage,
said opening of said internal passage being only partially obstructed by said valve member or not obstructed at all in said open position, thus permitting flow of gas through said internal passage,
wherein said retainer washer contacts said sleeve in said open position to prevent said valve member and said resilient bias member from traversing further proximally when said demand valve transitions from said closed position to said open position.

2. The demand gas valve apparatus of claim 1, further comprising:
said internal passage further including arcuately-shaped flow passages disposed through said transverse divider wall, said valve member fully obstructing said arcuately-shaped flow passages in said closed position.

3. The demand breathing circuit system of claim 1, further comprising:
said internal passage further including supplemental flow passages disposed through said transverse divider wall, said valve member fully obstructing said supplemental flow passages in said closed position.

4. The demand gas valve apparatus of claim 1, further comprising:
said resilient bias member being a spiral or compression spring having a first end and a second opposed end,
said spring being disposed around said stem with a proximal end of said spring engaging or otherwise disposed adjacent to said transverse divider wall.

5. The demand gas valve apparatus of claim 4, further comprising:
said spring having a stiffness sufficient to withstand external pressure and forces until an activating negative pressure of about −1 cmH$_2$O to about −10 cmH$_2$O is present within said proximal compartment.

6. The demand gas valve apparatus of claim 1, further comprising:
said stem of said valve member including a pair of tangs, each tang having a barb that defines a retention ledge that is disposed a spaced distance away from said distal tip, said retainer washer coupled to said stem by sitting on said retention ledge of said each tang, wherein said barb of said each tang is disposed through a central aperture of said retainer washer.

7. The demand gas valve apparatus of claim 1, further comprising:
an O-ring positioned between said piston and said valve seat in said closed position.

8. The demand gas valve apparatus of claim 1, further comprising:
an axial stop projection extending within said proximal compartment and engaging said valve member, said axial stop projection stopping said valve member from traversing further proximally when said demand valve is transitioning from said closed position to said open position.

9. A demand valve apparatus, comprising:
a housing formed of a proximal compartment and a distal compartment;
a transverse divider disposed between said proximal compartment and said distal compartment;
a valve member slidably positioned within said housing and formed of a piston and a stem;
a stopper positioned at or near a distal end of said stem of said valve member;
a resilient bias member in communication with said stem of said valve member, wherein a distal end of said resilient bias member is in communication with said stopper; and
a sleeve disposed around said stem of said valve member;
wherein said demand valve apparatus has a closed position and an open position,
wherein said closed position includes a spaced distance between said stopper and said sleeve and further includes a sealing disposition between said piston and said transverse divider,
wherein said open position includes a sealing disposition between said stopper and said sleeve and further includes a spaced distance between said piston and said transverse divider,
wherein a transition from said closed position to said open position results from negative pressure in said proximal compartment of said housing, causing proximal axial movement of said valve member due to said resilient bias member, such that gas can pass from said distal compartment to said proximal compartment through an internal passage of said housing.

10. The demand gas valve apparatus of claim 9, wherein said stopper is a retainer washer positioned around said distal end of said stem of said valve member.

11. The demand gas valve apparatus of claim 9, wherein in said closed position:
said resilient bias member is not under any stress or force, such that said resilient bias member maintains said valve member as a default position, and
said piston is positioned in said proximal compartment directly adjacent to said transverse divider wall, such that said piston engages said transverse divider wall to fully obstruct said internal passage, thus preventing flow of gas through said internal passage.

12. The demand gas valve apparatus of claim 11, wherein in said open position:
said resilient bias member is under a stress or force caused by said negative pressure, and
said opening of said internal passage is only partially obstructed by said valve member or not obstructed at all, thus permitting flow of gas through said internal passage.

13. The demand gas valve apparatus of claim 9, wherein a proximal end of said resilient bias member engages or is otherwise disposed adjacent to said transverse divider wall, and
a distal end of said resilient bias member engages or is positioned directly adjacent to said retainer washer, such that said resilient bias member is maintained on its proximal end by said transverse divider wall and on its distal end by said retainer washer.

14. The demand gas valve apparatus of claim 9, wherein said internal passage further includes arcuately-shaped flow passages disposed through said transverse divider wall, said valve member fully obstructing said arcuately-shaped flow passages in said closed position.

15. The demand breathing circuit system of claim 9, wherein said internal passage further includes supplemental flow passages disposed through said transverse divider wall, said valve member fully obstructing said supplemental flow passages in said closed position.

16. The demand gas valve apparatus of claim 9, wherein:
said resilient bias member is a spiral or compression spring having a first end and a second opposed end, and
said spring is disposed around said stem with a proximal end of said spring engaging or otherwise disposed adjacent to said transverse divider wall.

17. The demand gas valve apparatus of claim 9, wherein said stem of said valve member includes a pair of tangs, each tang having a barb that defines a retention ledge that is disposed a spaced distance away from said distal tip, said stopper coupled to said stem by sitting on said retention ledge of said each tang, wherein said barb of said each tang is disposed through a central aperture of said stopper.

18. The demand gas valve apparatus of claim 9, further comprising an O-ring positioned between said valve member and said transverse divider wall in said closed position.

19. The demand gas valve apparatus of claim 9, further comprising an axial stop projection extending within said proximal compartment and engaging said valve member, wherein said axial stop projection stops said valve member from traversing further proximally when said demand valve is transitioning from said closed position to said open position.

* * * * *